(12) United States Patent
De La Barrera et al.

(10) Patent No.: US 6,569,169 B2
(45) Date of Patent: May 27, 2003

(54) DEVICE FOR DETECTING OR FOLLOWING THE POSITION OF A BONE

(75) Inventors: José Moctezuma De La Barrera, Freiburg (DE); Markus J. Böhringer, Ehrenkirchen (DE)

(73) Assignee: Stryker Leibinger GmbH & Co KG, Freiburg (DE)

( * ) Notice: Subject to any disclaimer, the term of this patent is extended or adjusted under 35 U.S.C. 154(b) by 85 days.

(21) Appl. No.: 09/974,353

(22) Filed: Oct. 10, 2001

(65) Prior Publication Data

US 2002/0049377 A1 Apr. 25, 2002

(30) Foreign Application Priority Data

Oct. 11, 2000 (EP) .............................................. 00121374

(51) Int. Cl.[7] .............................................. A61B 17/58
(52) U.S. Cl. ........................ 606/102; 606/130; 600/407
(58) Field of Search ............................. 606/102, 99, 90, 606/105, 130, 86, 53; 600/232, 235, 407, 424, 427; 128/903; 340/870.07, 573

(56) References Cited

U.S. PATENT DOCUMENTS

| | | | | |
|---|---|---|---|---|
| 2,631,585 A | | 3/1953 | Siebrandt ..................... 128/92 |
| 5,279,309 A | * | 1/1994 | Taylor et al. ................ 600/595 |
| 5,807,252 A | * | 9/1998 | Hassfeld et al. ............. 600/407 |
| 5,951,564 A | * | 9/1999 | Schroder et al. ............. 606/100 |
| 6,490,467 B1 | * | 12/2002 | Bucholz et al. ............. 600/407 |

FOREIGN PATENT DOCUMENTS

| | | |
|---|---|---|
| DE | 295 03 001.1 | 5/1995 |
| WO | WO 96/11624 | 4/1996 |
| WO | WO 99/15097 | 4/1999 |

OTHER PUBLICATIONS

European Search Report dated Mar. 7, 2001, Appl. No. EP00121374.

English Language Abstract of DE 295 03 001.1.

\* cited by examiner

*Primary Examiner*—Pedro Philogene
(74) *Attorney, Agent, or Firm*—McCracken & Frank (57) ABSTRACT

A device for detecting or following the position of a bone is described. The device comprises a holder (10) for a position indicator, and a gripping mechanism (20, 30) for fastening the holder (10) to the bone. The gripping mechanism (20, 30) is designed to surround the bone on two opposite sides and on a further, third side and executes a constrained movement in the direction of the third side as the bone is being surrounded by the gripping mechanism (20, 30) on the two opposite sides.

16 Claims, 7 Drawing Sheets

DEVICE FOR DETECTING OR FOLLOWING THE POSITION OF A BONE

BACKGROUND OF THE INVENTION

The invention relates to a device for detecting or following the position of a bone according to the preamble of claim 1. The invention further relates to a system which includes this device.

In medical operations, it is necessary in certain circumstances to obtain data on the internal structures of the body prior to the operation, for example by means of a CT scan or an MRI scan, and then to make this data available to the operating physician during the operation, for example on a monitor. The problem is that, during the operation, the internal structures of the body may be displaced, for instance, by the respiratory movements of the patient or by the surgical intervention of the physician. A displacement of a bone, however, means that the previously recorded images no longer represent the actual position of the bone and as a result during a surgical intervention the physician may plan the wrong approach.

Devices which measure a movement of a part of the body and determine and follow the instantaneous position of the part of the body are known. These devices work with position indicators in the form of, for example, radiation emitters which are fastened to supporting frames. The supporting frames in turn are secured to the part of the body. In practice, it has turned out that although the fastening of position transmitters to such frames permits position determination of the frame and thus also position determination of the part of the body held in the frame, the accuracy of such position determination is in need of improvement since the supporting frames are not fastened to the bone directly but, for example, to the head or to the arm. Moreover, slight displacements between the part of the body and the frame cannot be ruled out with certainty.

In order to avoid the problems associated with such frames, DE 295 03 001 proposes dispensing with the frame and instead of this fixing the position indicators directly to the bone with the aid of bone screws. The bone screws in this case have a screw body which acts as a holder for the position indicator.

However, the device for detecting or following the position of a bone known from DE 295 03 001 also has a series of disadvantages. For instance, both the fastening and the release of the bone screws are associated with expenditure in terms of time and apparatus. This problem is particularly pronounced when the screws have to be placed inside the patient's body. Moreover, owing to the impairment of the bone caused by the screwing-in, it is not possible to use bone screws as a holder for the position indicators in a large number of applications. A use of the device known from DE 295 03 001 inside the patient's body is also frequently excluded because the position indicators, in the form of light-emitting diodes, received by the bone screws are difficult to see or cannot be seen at all during the operation. For this reason, the device known form DE 295 03 001 is in practice only suitable for detecting and following the position of a cranial bone.

SUMMARY OF THE INVENTION

The object on which the invention is based is to provide a device for detecting or following the position of a bone which can be fastened to a bone, in particular inside the body, and detached therefrom again in a simple yet reliable manner. Furthermore, the device is to be capable of being designed so as to simplify the detection of the signal emitted by the position indicator especially when the device is fastened to a bone situated inside the body. A further object finally is to specify a system for detecting and/or following the position of a bone which includes the device according to the invention.

These objects are solved by a device according to claim 1 and a system according to claim 13. The subclaims relate to advantageous refinements and developments of the invention.

According to the invention, in the case of a device for detecting or following the position of a bone, which comprises a holder for a position indicator, there is provided a gripping mechanism which is designed to surround the bone on two opposite sides and on a third side, and which executes a constrained movement in the direction of the third side as a result of the bone being surrounded on the two opposite sides. By means of the gripping mechanism, an optimum support at three or more points and an optimum flow of force is thus achieved in that, upon surrounding the bone on the two opposite sides, assisting kinematics ensure that the device is pressed against the bone on the third side.

The gripping mechanism allows fastening and detachment of the holder without the bone being damaged. In contrast to bone screws for example, the device can be fastened to the bone without an additional tool. This reduces on the one hand the expenditure in terms of apparatus for fastening and detaching the holder and on the other hand also the expenditure in terms of time associated with the fastening and detaching. Since the fastening of the holder to the bone is generally associated with a surgical intervention, the operating time is thus also shortened.

The gripping mechanism is preferably designed in such a manner that it comprises a pivoting mechanism with, for example, two or more pivotable gripping elements which cooperate with one or more further gripping elements in such a manner that the bone is surrounded on three or more sides by the set of gripping elements as a whole. An actuating device can be provided for the pivotable gripping elements. This actuating device allows the pivotable gripping elements to move relative to the bone and to the at least one further gripping element. Advantageously, the actuating device additionally allows the pivotable gripping elements to be locked in a position surrounding the bone.

The cooperation between a pivotable gripping element and the actuating mechanism takes place particularly preferably in such a manner that an at least regionally wedge-shaped element acts on a pivotable gripping element or on a plurality of pivotable gripping elements simultaneously. In this way, by movement of the wedge element the pivotable gripping elements can be actuated. It is also conceivable to use the wedge element to lock the pivotable gripping elements with a preset clamping force in a position surrounding the bone in order thereby to connect the holder for the position indicator firmly to the bone. A simple and reliable connection between the bone and the device for detecting or following the bone is thus ensured.

In a preferred refinement of the gripping mechanism, each pivotable gripping element is designed as a lever arm which is part of a rotatably mounted lever. The actuating mechanism can then cooperate, for example by means of the wedge element, with this lever arm or with one or more further lever arms of the lever.

A further refinement of the device provides for the holder for the position indicator to have an elongate portion which spatially separates the gripping elements from an operating element of the actuating device for the gripping elements. For instance, it is conceivable to arrange the gripping elements in the region of one end of the elongate portion of the gripping elements and to provide the operating element for the actuating device in the region of the opposite end. Such a refinement of the holder for the position indocator allows the operating element to be arranged spatially remote from the bone. This is expedient especially in surgical interventions, since a sufficient length of the elongate portion means that the operating element can protrude from the patient's body. For the same reason, it is advantageous to fasten the position indicator likewise in the region of the operating element, i.e. at the end of the holder opposite the gripping elements.

BRIEF DESCRIPTION OF THE DRAWINGS

Further advantages and refinements of the invention emerge from the exemplary embodiment and the figures, in which.

DETAILED DESCRIPTION OF THE INVENTION

Figure 1:
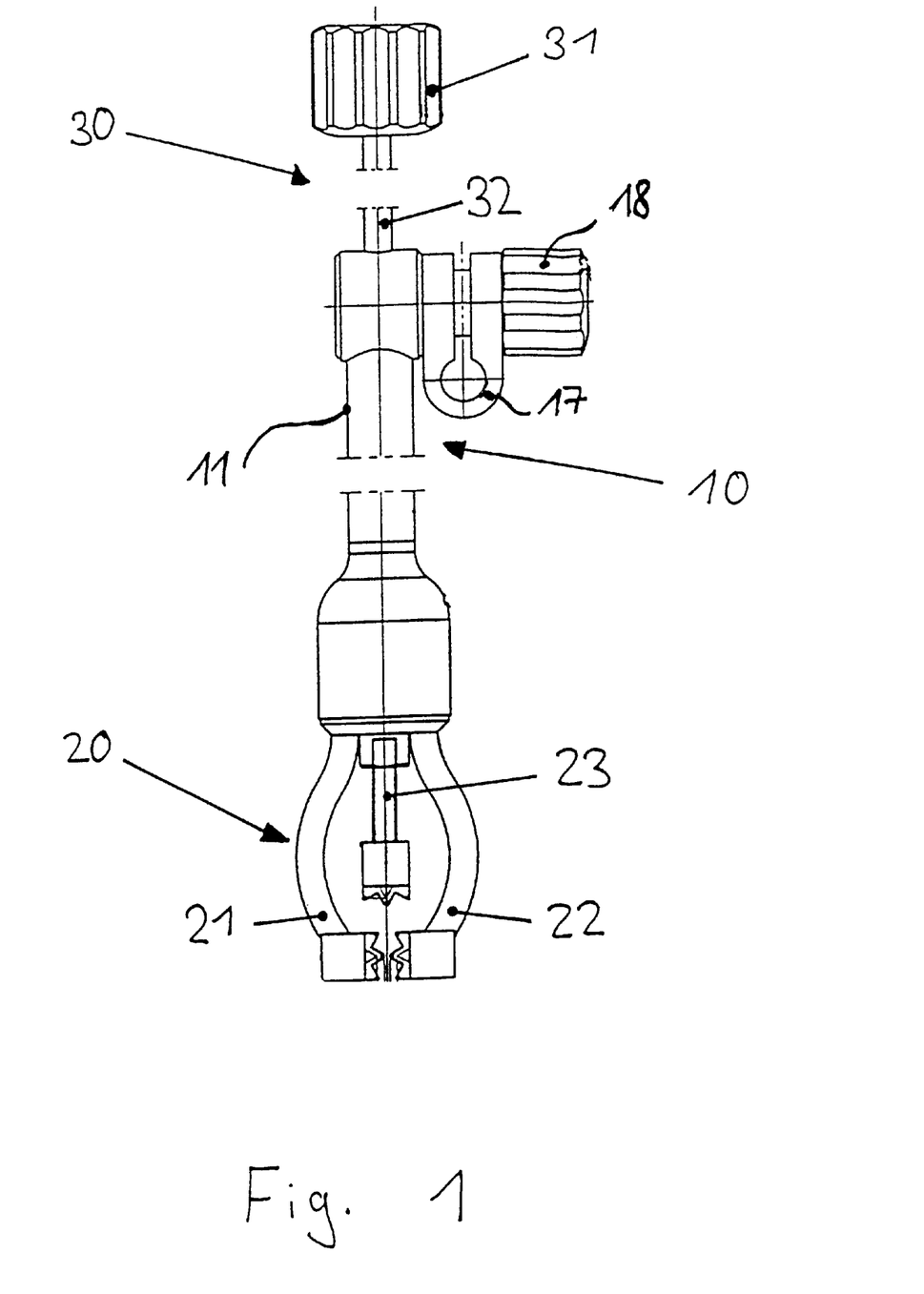
FIG. 1 shows a side view of the device according to the invention.

In FIG. 1 an exemplary embodiment of a device for detecting or following the position of a bone is illustrated in a side view. The device comprises a holder 10 for a position indicator, and a gripping mechanism 20, 30. The gripping mechanism comprises a plurality of gripping elements 20 and an actuating device 30 for a pivoting mechanism comprising two pivotable gripping elements 21, 22. The actuating device 30 in turn has an operating element in the form of a rotary handle 31. The rotary handle 31 is connected in a rotationally fixed manner to a shaft 32 of the actuating device 30.

In the case of the exemplary embodiment illustrated in FIG. 1, the plurality 20 of gripping elements is formed by three gripping elements 21, 22 and 23. The two pivotable gripping elements 21, 22 are each designed as part of a lever cooperating with the actuating device 30. The third gripping element 23 is fixedly connected to the holder 10. A bone can be surrounded on three sides by the three gripping elements 21, 22 and 23.

As can be seen from FIG. 1, the holder 10 has an elongate structural form. The rotary handle 31 of the actuating device 30 is arranged at one end of the holder 10 and the plurality 20 of gripping elements is situated in the region of the opposite end of the holder 10.

Figure 2:
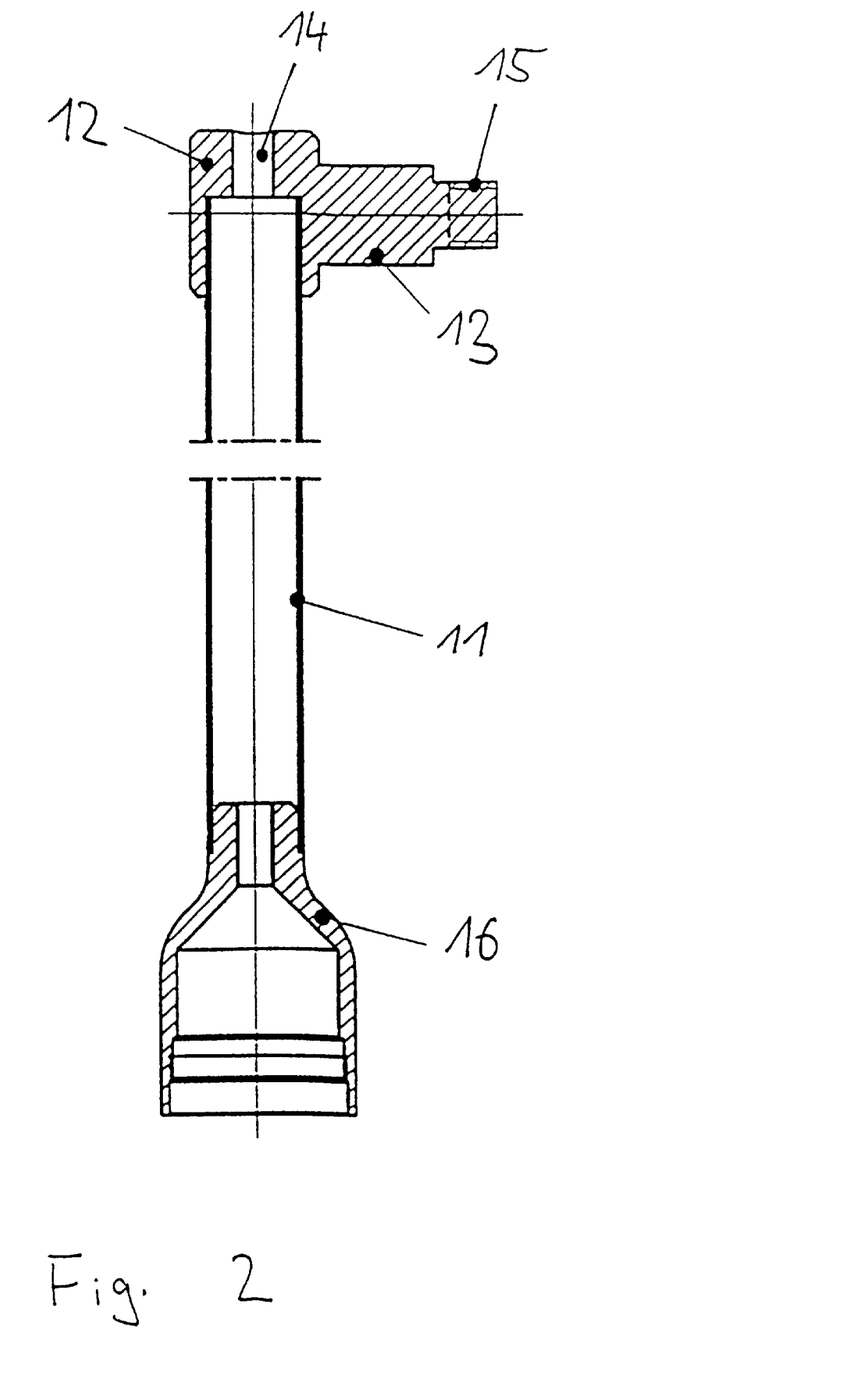
FIG. 2 shows the holder for a position indicator, in cross-section.

The holder 10 is illustrated in cross-section in FIG. 2. The holder 10 comprises an elongate portion in the form of a sleeve 11 designed as a hollow cylinder. The length of the sleeve 11 essentially determines the distance between the rotary handle 31 and the gripping elements 21, 22 and 23.

Arranged on the upper end of the sleeve 11 is a cap 12. This cap 12 comprises a cylindrical extension 13, extending in the radial direction with respect to the sleeve 11, for fastening a position indicator. Arranged at the end of the cylindrical extension 13 is a further cylindrical portion 15 of smaller diameter, which is provided with a thread. The cap 12 further has a central bore 14, through which, as illustrated in FIG. 1, the shaft 32 extends.

At an end of the sleeve 11 opposite the cap 12, the sleeve 11 is connected to a housing 16. The housing 16 has essentially the shape of a hollow cylinder with a larger cross-section than the sleeve 11. The interior of the housing 16 has a portion tapering conically in the direction of the sleeve 11.

Cap 12, sleeve 11 and housing 16 are connected to one another by laser welding. It is however also conceivable to connect the cap 12 to the sleeve 11 in such a manner that the cap 12 is pivotable about the longitudinal axis of the sleeve 11. Furthermore, sleeve 11, cap 12 and housing 16 may also be designed in one piece.

Figure 3:
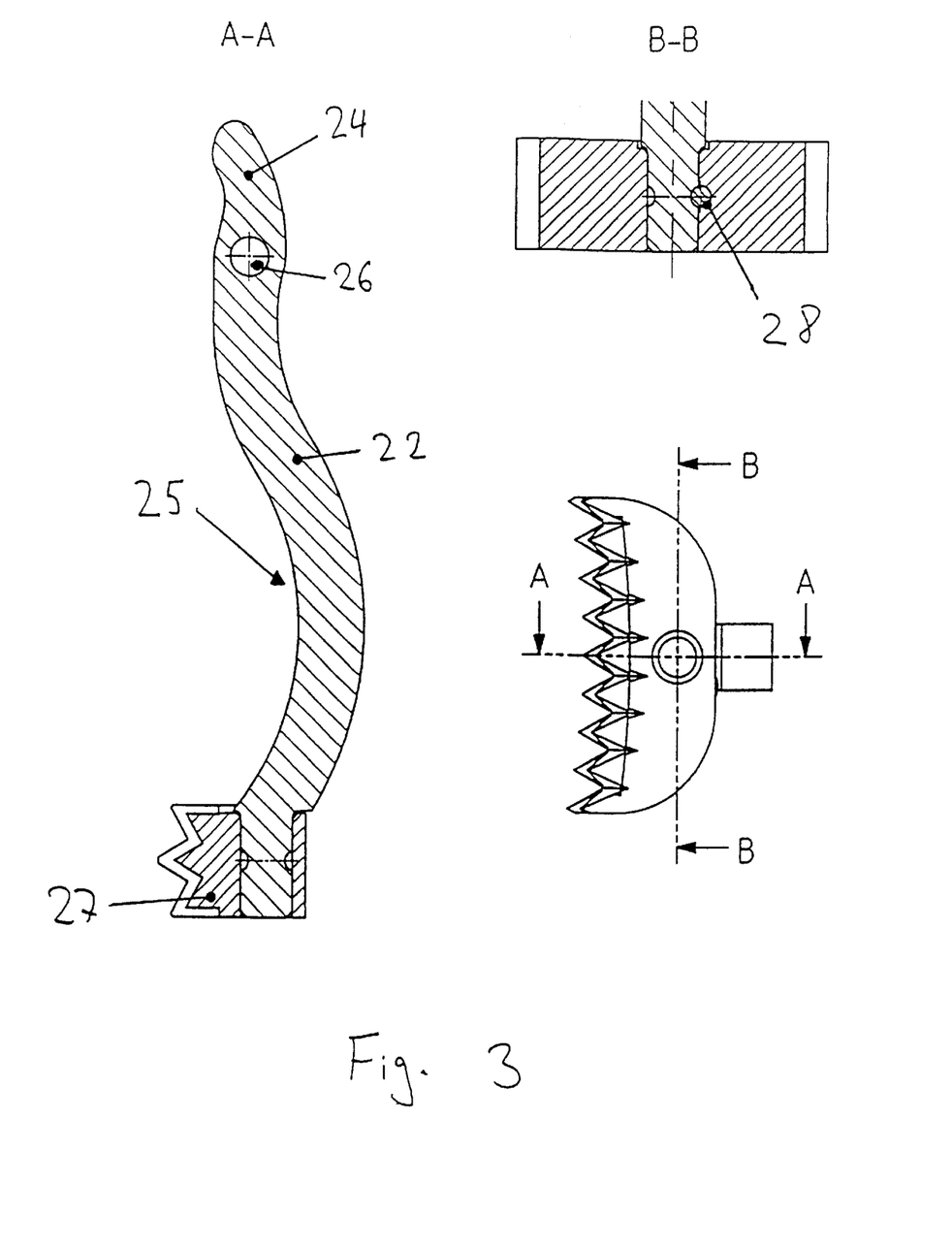
FIG. 3 shows a gripping element, in plan view and in cross-sections.

In FIG. 3 the design of the pivotable gripping element 22 is illustrated in plan view and in two sections. According to FIG. 3, the movable gripping element 22 is designed as part of a lever 25. The lever 25 has a curved first lever arm forming the gripping element 22, at the end of which a jaw 27 is arranged (section A—A). The lever 25 further comprises a second lever arm 24 cooperating with the actuating device for the gripping elements. Arranged between the first lever arm 22 and the second lever arm 24 is a bore 26 for mounting the lever 25.

The jaw 27 is equipped with teeth which ensure a reliable connection between the gripping element 22 and the bone. To assist this aim, the jaw 27 is designed to be rotatable about the lever longitudinal axis. As can be seen from the section B—B, the jaw 27 is rotatably connected to the lever 22 with the aid of a screw 28. According to an alternative embodiment, the jaw 27 can however also be connected in a rotationally fixed manner to the lever 22.

Figure 4:
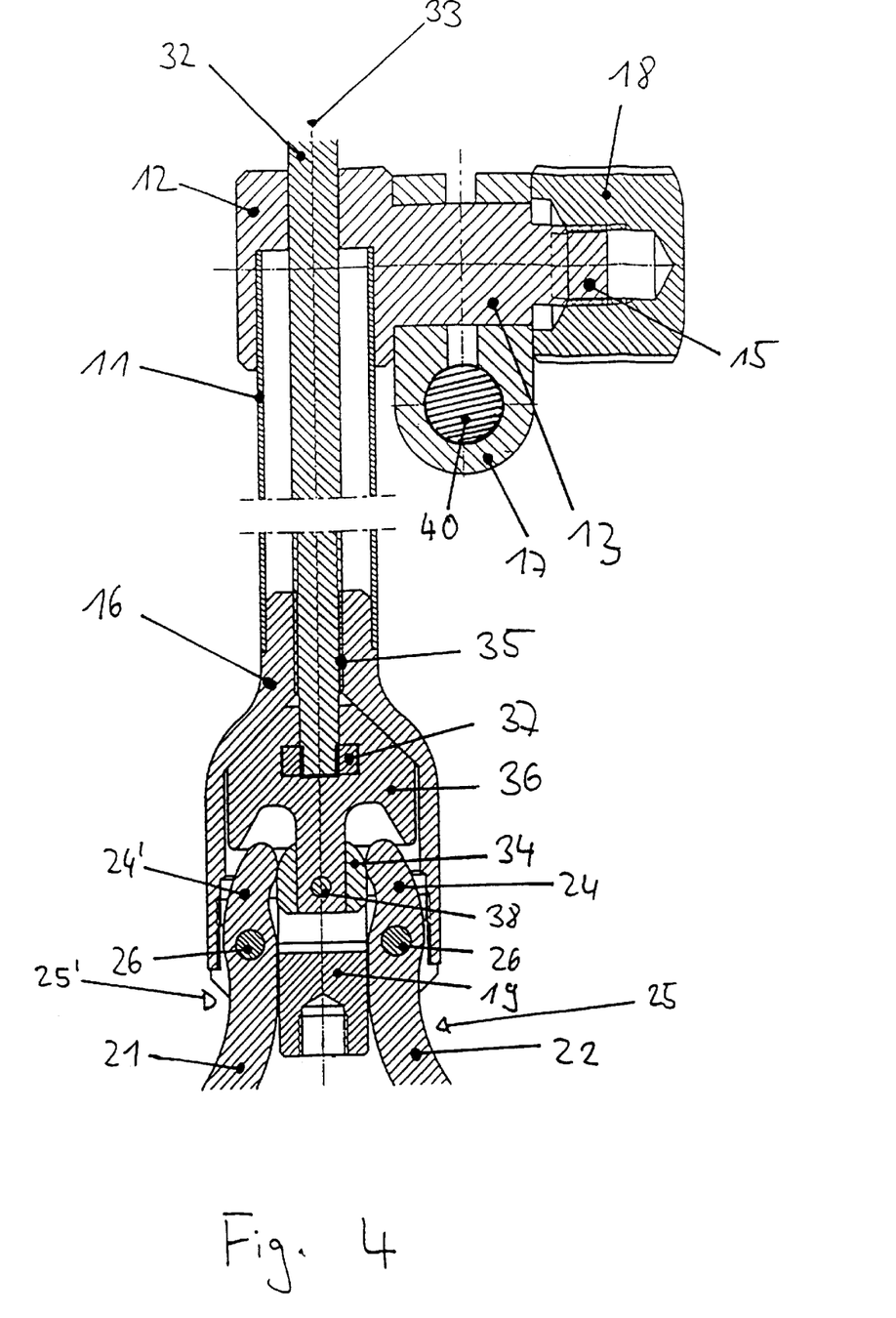
FIG. 4 shows the actuating mechanism for the gripping elements in a position surrounding the bone.

In FIG. 4 one possibility for fastening a position indicator 40 to the holder 11 is illustrated. The position indicator 40 is connected to the holder 11 via a clamp 17 seated on the cylindrical extension 13 of the cap 12. The clamp 17 can be actuated with the aid of a locking device for the clamp 17 in the form of a nut 18 cooperating with the thread of the cylindrical portion 15. By moving the nut 18 in the direction of the sleeve 11, the position indicator 40 is firmly surrounded by the clamp 17. By moving the nut 18 in the opposite direction, the position indicator 40 is released again.

In FIG. 4, furthermore, the position and functioning of the actuating device when the pivotable gripping elements 21, 22 are embracing a bone is sketched. The actuating device comprises a wedge-shaped element 34 coupled to a shaft 32. The shaft 32 in turn is guided in a thread 35 formed in the region of a neck of the housing 16 adjoining the sleeve 11. By rotation of the shaft 32 about the shaft longitudinal axis 33, the wedge element 34 can be displaced axially with respect to the shaft longitudinal axis 33.

The wedge element 34 cooperates with the two second lever arms 24, 24' of the two levers 25, 25'. The wedge element 34 engages in an indentation of the second lever arms 24, 24' for this purpose. The engagement in the indentation of the two lever arms 24, 24' has the effect of moving the ends of the two lever arms 24, 24' away from each other by displacement of the wedge element 34 upwards, i.e. in the direction of the cap 12. This pushing-apart of the ends of the lever arms 24, 24' by the wedge element 34 in turn has the effect of moving the jaws of the pivotable gripping elements 21, 22 towards each other to surround a bone. The cooperation of thread 35, shaft 32 and the wedge element 34 contacting the second lever arms 24, 24' achieves a situation where the pivotable gripping elements 21, 22 can be locked in a position firmly surrounding the bone.

The wedge element 34 is coupled to the shaft 32 via a component 36 tapering conically in the direction of the cap 12. For this purpose, the conical component 36 has a peg-shaped extension which extends along the shaft longitudinal axis 33 in the direction of the gripping elements 21, 22, 23 and to which the annular wedge element 34 is connected by a pin 38. The shaft 32 has, at an end opposite the rotary handle, a ring 37 fixedly connected to the shaft 32. This ring 37 in turn is rotatably mounted in a recess of the conical component 36. In this way, the rotary movement of the shaft 32 is uncoupled from the movement of the conical component 36 and of the wedge element 34 axially with respect to the shaft longitudinal axis 33. The rotary movement of the shaft 32 is therefore not transmitted to the conical component 36 and the wedge element 34. Although the described connection between shaft 32, conical component 36 and wedge element 34 is preferred, it would be conceivable in principle to construct these three elements in one piece.

Upon axial movement of the conical component 36, the latter is able to cooperate with the conical recess of the housing 16. In this way, a self-centring of the actuating device is achieved.

The housing 16 is closed, on its side opposite the sleeve 11, by a cover 19. According to the exemplary embodiment in FIG. 4, a screw connection is provided between the housing 16 and the cover 19. The levers, 25, 25' are rotatably mounted in the cover 19. This is effected with the aid of pins inserted into the bores 26 of the levers 25, 25'.

The cover 19 has a peg-shaped extension extending along the shaft longitudinal axis 33 in the direction of the bone. This extension is provided with a blind-hole bore which has an internal thread and acts as a receptacle for a fixed gripping element. This situation is illustrated for the fixed gripping element 23 in FIG. 1. In an alternative design of the device illustrated in FIG. 4, either the receptacle for the fixed gripping element 23 or the fixed gripping element 23 or both are height-adjustable. This means that the receptacle or the gripping element 23 or both are movable axially with respect to the shaft longitudinal axis 33.

Figure 5:
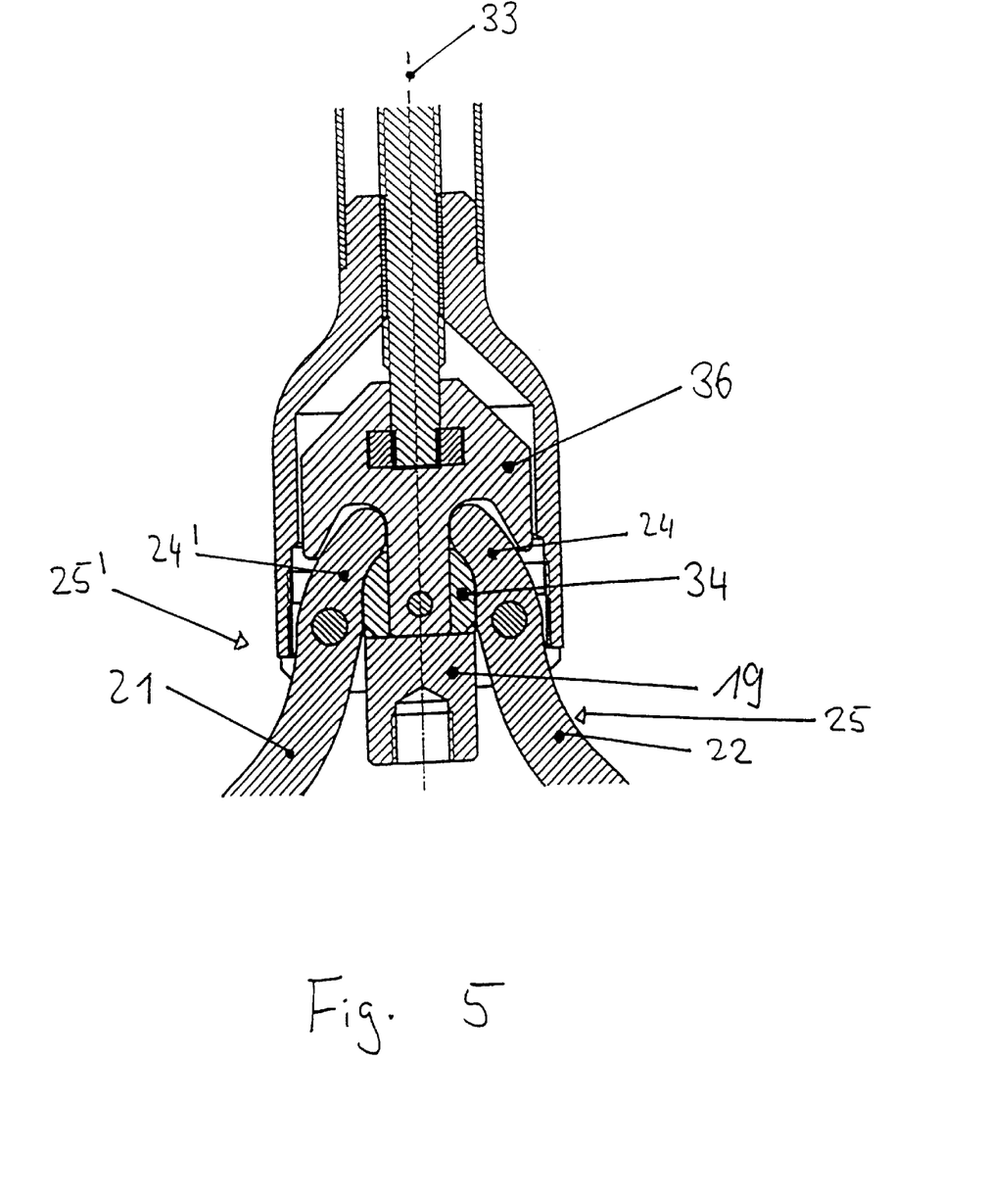
FIG. 5 shows the actuating mechanism for the gripping elements in an open position.

In FIG. 5 the actuating device is illustrated in an open state. As soon as the wedge element 34 is moved in the direction of the cover 19 by rotation of the shaft 32, the ends of the second lever arms 24, 24' are no longer pushed apart and as a result the ends of the first lever arms 25, 25' are no longer pushed towards each other. In this position of the wedge element 34, the bone surrounded by the gripping elements is therefore released again.

Figure 6:
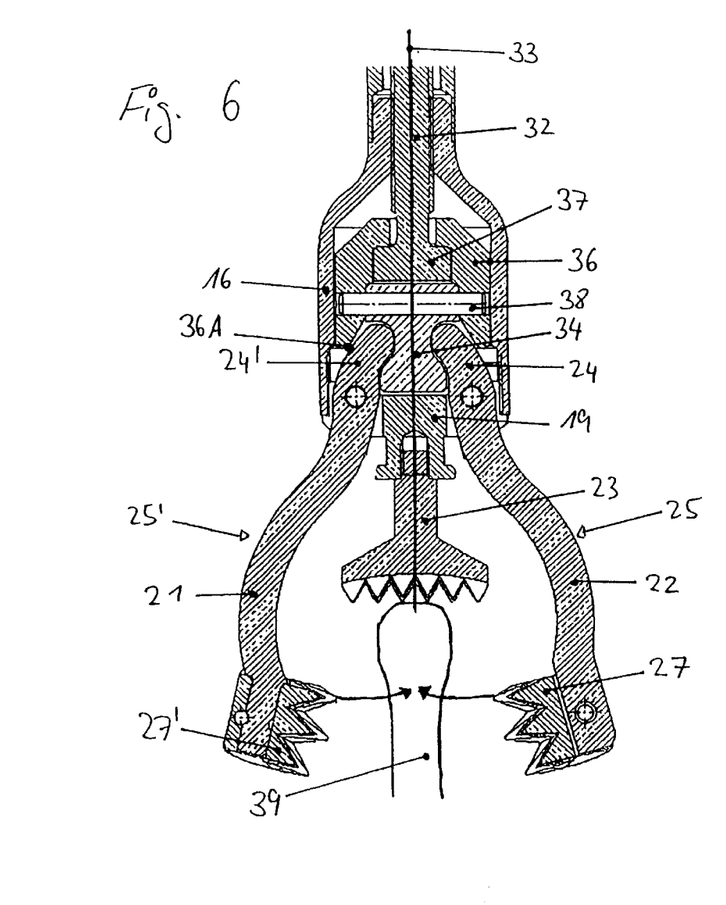
FIGS. 6 and 7 show the fastening of the device according to the invention on the spinous process of a vertebral body.
Figure 7:
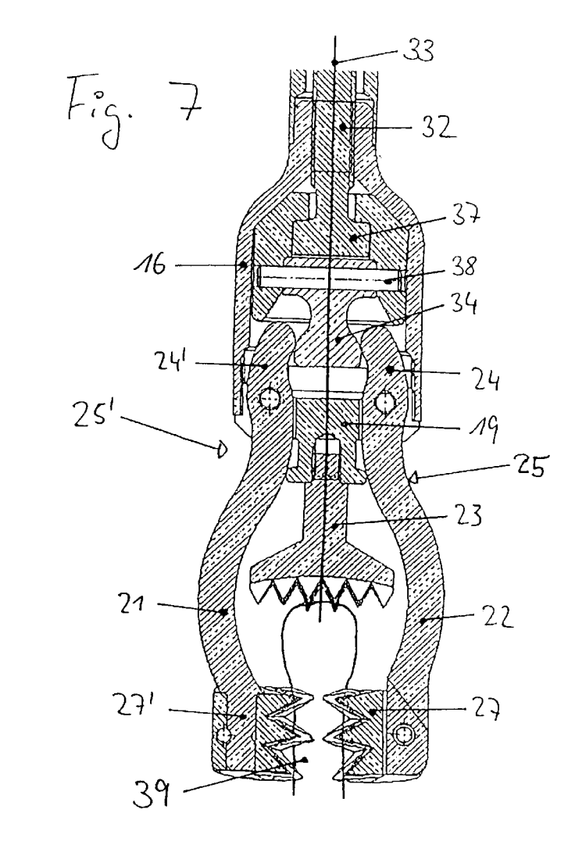

In FIGS. 6 and 7 the fastening of the device according to the invention on the spinous process 39 of a vertebral body is illustrated by way of example. The device illustrated in FIGS. 6 and 7 differs from the device illustrated in FIGS. 4 and 5 in the coupling of the wedge element 34 to the shaft 32. The wedge element 34 is not designed as a ring arranged on a peg-shaped extension of the conical component 36 extending in the direction of the bone as in the case of the device illustrated in FIGS. 4 and 5, but as a solid component. Furthermore, in the case of the device illustrated in FIGS. 6 and 7, the ring 37 mounted in a recess of the conical component 36 is designed in one piece with the shaft 32.

In FIG. 6 the device for detecting or following the position of a vertebral body is placed in the open position around a spinous process 39 of the vertebral body. By rotation of the shaft 32, the wedge element 34 has been brought into contact with the cover 19. The wedge element 34 and the conical component 36 are thus situated in their lowermost position with respect to the housing 16. Upon movement into this position, the radially inner edge 36A of an annular end face, facing towards the spinous process 39, of the conical component 36 cooperates with the second lever arms 24, 24' of the two levers 25, 25' in such a manner that the ends, facing away from the spinous process 39, of the second lever arms 24, 24' are displaced radially inwards with respect to the longitudinal axis 33. Consequently, those ends of the two pivotable gripping elements 21, 22 which bear the jaws 27, 27' are moved radially outwards. In this position the device is now placed onto the spinous process 39 in such a manner that the teeth of the fixed gripping element 23 contact the upper side, facing towards the device, of the spinous process 39.

If the conical component 36 and the wedge element 34 coupled to the conical component 36 are displaced upwards with respect to the housing 16 by rotation of the shaft 32, the wedge element 34 cooperates with the two ends, facing away from the spinous process 39, of the second levers arms 24, 24' in such a manner that these ends are moved radially outwards with respect to the longitudinal axis 33. Consequently, the two pivotable gripping elements 21, 22, each forming the first lever arms of the levers 25, 25', execute a pivoting movement in the direction of the spinous process 39 and approach the latter, as illustrated in FIG. 7, from two opposite sides. Owing to this pivoting movement of the two pivotable gripping elements 21, 22, a constrained movement of the fixed gripping element 23 in the direction of the third side of the spinous process 39 takes place.

This constrained movement is attributable to the fact that the two pivotable gripping elements 21, 22 approach the spinous process 39 on a curved path. As a result of the curved path, the upper row of teeth of each of the jaws 27, 27' contacts the spinous process 39 first. If the upper rows of teeth now come into contact with the spinous process 39, a further movement of the second lever arms 24, 24' radially outwards produces a pulling movement of the fixed gripping element 23 in the direction of the surface, facing towards this gripping element 23, of the spinous process 39. This pulling movement ends only when all the rows of teeth of the jaws 27, 27' contact the spinous process 39. The teeth, facing towards the spinous process 39, of the fixed gripping element 23 therefore penetrate into the spinous process 39 slightly. The device consequently surrounds the process 39 reliably on three sides, a particularly firm connection being ensured owing to the penetration of the teeth of the fixed gripping element 23 into the spinous process 39.

The described device is preferably employed in a system for detecting or following the position of a bone. Such a system is illustrated schematically in FIG. 8. In this system, a position indicator 40, for example a radiation source emitting electromagnetic radiation 41, is arranged in the holder of the device. Radiation sources which emit light in the visible wavelength range are preferably employed. Suitable examples are light-emitting diodes or laser diodes.

Figure 8:
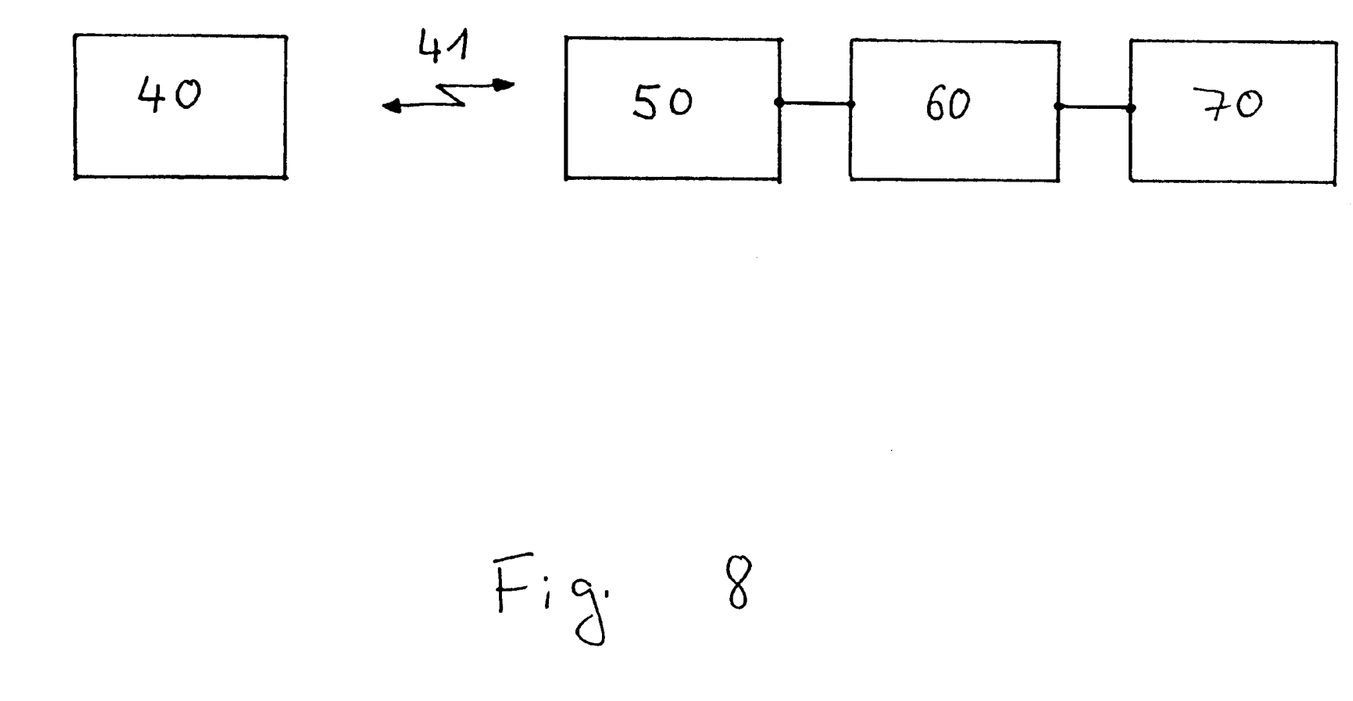
FIG. 8 shows a system for detecting or following the position of a bone.

The system comprises a detector 50 for detecting a signal emitted by the position transmitter 40. Also part of the system is an evaluating unit 60 which, on the basis of an output signal of the detector 50 and a previously produced patient image, performs a comparison of the current position of the bone and the position of the bone on the patient image. The evaluating unit 60 can then generate a new patient image showing the bone in its current position. This image is then made available to the operating physician via a monitor or another display unit 70.

What is claimed is:

1. A device for detecting or following a position of a bone, with a holder for a position indicator, wherein, for fastening the holder to the bone, a gripping mechanism is provided which surrounds the bone on two opposite sides and on a third side, and wherein the gripping mechanism is designed to execute a constrained movement in the direction of the third side as a result of the bone being surrounded on the two opposite sides.

2. The device according to claim 1, wherein the gripping mechanism has a pivoting mechanism for surrounding the bone on the two opposite sides.

3. The device according to claim 2, wherein the pivoting mechanism comprises two pivotable gripping elements.

4. The device according to claim 3, wherein the gripping mechanism comprises a third gripping element which is fixed or movable along a longitudinal axis of the device.

5. The device according to claim 2, wherein the gripping mechanism comprises an actuating device for the pivoting mechanism.

6. The device according to claim 5, wherein the holder comprises an elongate portion with two opposite ends, the gripping mechanism being arranged in a region of a first end and the actuating device being operable in a region of a second end.

7. The device according to claim 6, wherein the holder has in the region of the second end an extension which extends in a radial direction with respect to the elongate portion and to which the position indicator can be fastened.

8. The device according to claim 3, wherein the pivotable gripping elements are each designed as a first lever arm of a rotatably mounted lever.

9. The device according to claim 8, wherein the first or a second lever arm of each lever cooperates with an actuating device for the pivoting elements.

10. The device according to claim 2, wherein an actuating device for the pivoting mechanism is provided and wherein the actuating device comprises a wedge element cooperating with at least one of the pivotable gripping elements.

11. The device according to claim 10, wherein the actuating device has a shaft guided in a thread, and wherein the wedge element is coupled to the shaft in such a manner that the wedge element, by rotation of the shaft about a shaft longitudinal axis, is movable axially with respect to the shaft longitudinal axis.

12. The device according to claim 6, wherein a holder for a third gripping element is provided in the region of the first end of the elongate portion, and wherein the holder for the third gripping element or a third gripping element arranged in the holder is height-adjustable.

13. A system for detecting or following a position of a bone having a device with a holder for a position indicator, the device having, for fastening to a bone, a gripping mechanism which surrounds the bone on two opposite sides and on a third side, and the gripping mechanism being designed to execute a constrained movement in the direction of the third side as a result of the bone being surrounded on the two opposite sides;

a detector for detecting a signal of the position indicator; and an evaluating unit which, on the basis of an output signal of the detector and a previously produced patient image, determines a deviation of a current position of the bone from a position of the bone on a patient image.

14. The system according to claim 13, wherein a patient image showing the current position of the bone can be generated by the evaluating unit on the basis of the previously produced patient image and the output signal of the detector, and wherein furthermore a display unit for displaying the patient image generated in this manner is provided.

15. A device for detecting or following a position of a bone, having:

a holder for a position indicator; and a gripping mechanism for fastening the holder to the bone, the gripping mechanism having a first device for surrounding the bone on two opposite sides and a second device for executing a constrained movement in the direction of a third side of the bone as a reaction to an actuation of the first device.

16. A device for detecting or following a position of a bone, including:

a holder for a position indicator; and a gripping device for surrounding the bone on at least three sides of the bone, the gripping device executing a coupled movement in the direction of a third one of the three sides as a reaction to the bone being surrounded on two opposite sides of the three sides.

* * * * *